United States Patent [19]

Schrader et al.

[11] Patent Number: 5,459,313
[45] Date of Patent: Oct. 17, 1995

[54] METHOD OF AND APPARATUS FOR OPTICALLY TESTING RADIATION TRANSMITTING CONTAINERS

[75] Inventors: Bernhard Schrader, Essen; Günter G. Hoffmann, Oberhausen, both of Germany

[73] Assignee: alfill Getränketechnik GmbH, Hamburg, Germany

[21] Appl. No.: 177,586

[22] Filed: Jan. 5, 1994

[30] Foreign Application Priority Data

Jan. 7, 1993 [DE] Germany .................. 43 00 169.6

[51] Int. Cl.$^6$ ............................................. G01N 21/90
[52] U.S. Cl. .................. 250/223 B; 356/240; 356/342; 209/524
[58] Field of Search .................. 250/223 B, 223 R, 250/226; 356/239, 240, 301, 326, 328, 330, 342; 209/524, 526

[56] References Cited

U.S. PATENT DOCUMENTS

| | | |
|---|---|---|
| 3,394,263 | 7/1968 | Baker . |
| 3,894,806 | 7/1975 | Remy et al. . |
| 4,030,827 | 6/1977 | Delhaye et al. . |
| 4,259,574 | 3/1981 | Carr et al. . |
| 4,488,648 | 12/1984 | Claypool . |
| 4,547,067 | 10/1985 | Watanabe . |
| 4,584,469 | 4/1986 | Lovalenti . |
| 4,606,634 | 8/1986 | Bieringer . |
| 4,778,999 | 10/1988 | Fisher . |
| 4,924,083 | 5/1990 | Ishikawa et al. . |
| 4,975,568 | 12/1990 | Taniguchi et al. .......... 250/223 B |
| 5,136,157 | 8/1992 | Apter et al. . |
| 5,141,110 | 8/1992 | Trischan et al. .............. 209/524 |
| 5,314,072 | 5/1994 | Frankel et al. .............. 209/524 |
| 5,318,172 | 6/1994 | Kenny et al. ............... 250/226 |

FOREIGN PATENT DOCUMENTS

| | | |
|---|---|---|
| 0056239 | 7/1982 | European Pat. Off. . |
| 0483966 | 5/1992 | European Pat. Off. . |
| 0493815 | 7/1992 | European Pat. Off. . |
| 1366923 | 1/1988 | U.S.S.R. . |
| 00862 | 2/1988 | WIPO . |
| 01378 | 2/1988 | WIPO . |
| 09390 | 10/1989 | WIPO . |

OTHER PUBLICATIONS

Von Risto Myllyla "Sehen, Fühlen, Kontrollieren", Technische Rundschau, 1991, pp. 46–49.

Günter Georg Hoffmann et al., "Combined Raman and Fluoroescence Spectroscopy with the Same Compact CCD-Based Instrument", Applied Spectroscopy, vol. 46, No. 4, 1992, pp. 568–570.

Primary Examiner—Edward P. Westin
Assistant Examiner—John R. Lee
Attorney, Agent, or Firm—Darby & Darby

[57] ABSTRACT

Light-transmitting plastic and/or glass bottles are tested at a station where selected portions of their internal surfaces scatter radiation issuing from a beam of monochromatic radiation. The scattered radiation is intercepted and monitored for the generation of signals which denote the presence or absence of impurities on the selected portions of the internal surfaces and/or certain substances in the walls adjacent the selected portions of the internal surfaces of tested bottles. Such signals are processed, and the processed signals are utilized to classify the bottles according to their defects and/or to segregate unsatisfactory bottles from acceptable bottles and/or to segregate glass bottles from plastic bottles and/or to classify satisfactory plastic bottles in accordance with the nature of their plastic materials. The scattered radiation can constitute Raman, Rayleigh and/or fluorescence radiation.

26 Claims, 1 Drawing Sheet

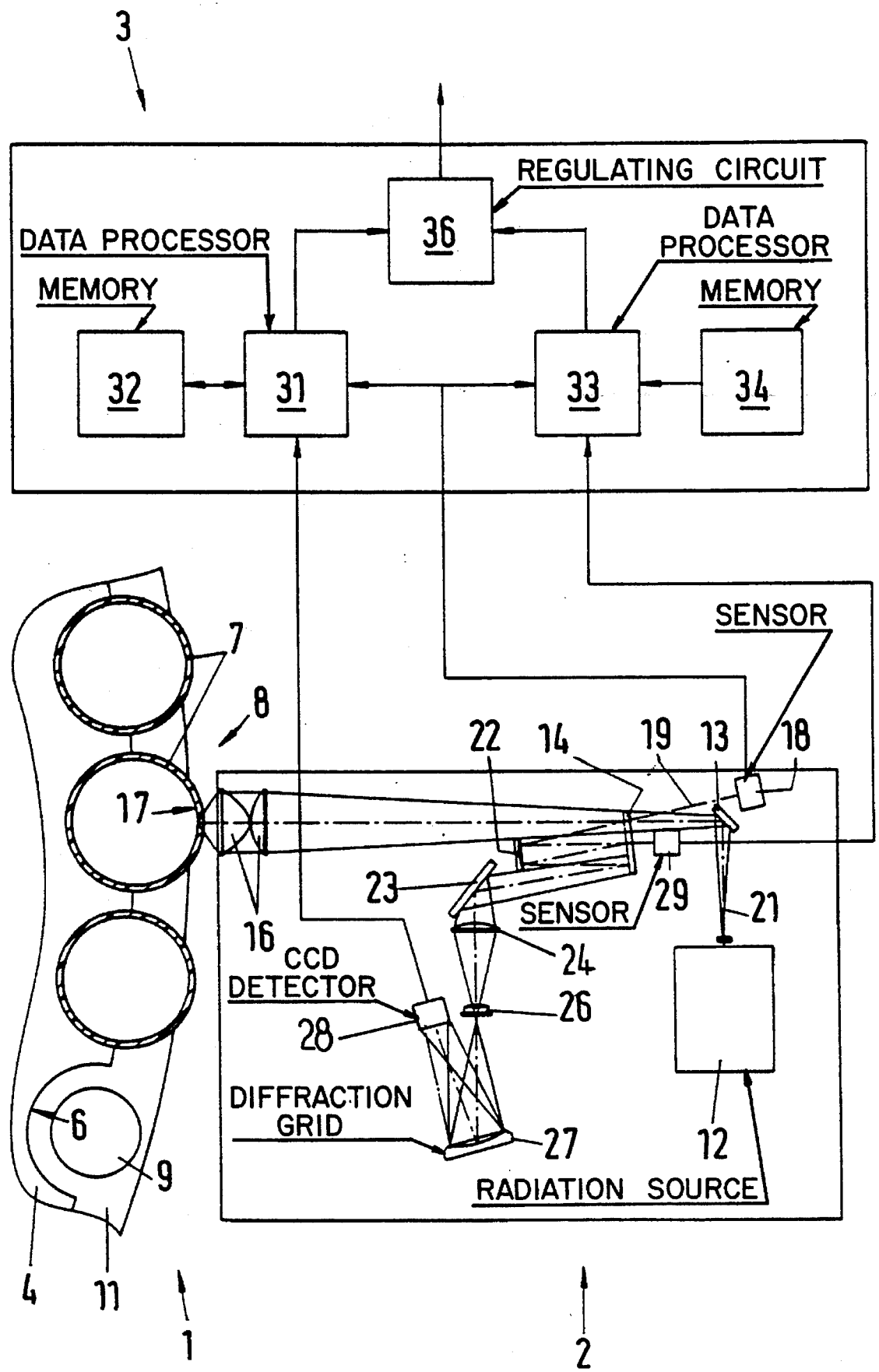

METHOD OF AND APPARATUS FOR OPTICALLY TESTING RADIATION TRANSMITTING CONTAINERS

BACKGROUND OF THE INVENTION

The present invention relates to improvements in methods of and in apparatus for testing containers, especially bottles which are made of glass or a synthetic plastic material. More particularly, the invention relates to improvements in methods of and in apparatus for testing containers (hereinafter called bottles for short) with beams of optical radiation. Still more particularly, the invention relates to improvements in methods of and in apparatus for optically testing preferably colorless bottles which transmit radiation and are transported through a testing station wherein a selected portion of the surface of each of a series of successive bottles is positioned to influence a beam of radiation so that the changes in the characteristics of such beam can be resorted to for the determination of one or more qualities of the tested bottle.

The beverage making and bottling industries utilize large numbers of plastic bottles, particularly those made of polyethylene terephthalate (PET). An advantage of such bottles is that they can be mass-produced with smooth internal surfaces. However, such bottles also exhibit a drawback, namely that they are capable of swelling. Such characteristics of a bottle which is made of PET are undesirable because various chemical substances whose chemical composition is similar to that of PET are likely to penetrate into the material of the bottle close to the internal surface and to settle between the long-chain molecules of the plastic material. This creates problems when a PET bottle is thereupon filled with a flowable substance, such as a beverage, containing one or more materials whose composition is similar to that of PET. For example, if a bottle was utilized to store waste oil, benzine or a herbicide, such substances (or certain constituents of such substances) are likely to be diffused and to settle in the intermolecular spaces within a wall of the bottle. If the same bottle is thereupon put to use as a means for storing a metered quantity of a beverage, even after very thorough cleaning prior to admission of the beverage, the diffused substances are likely to leave the intermolecular spaces and to render the confined beverage undrinkable or even dangerous to the health of the consumer. Furthermore, aromatic substances which are contained in fruit juices or other aromatized beverages are likely to penetrate into the wall of a PET bottle. This is not, or need not be, harmful or undesirable if the bottle is thereupon filled with the same beverage. However, the aromatic substances which have penetrated into the wall of a bottle are likely to undesirably affect the taste of a different beverage which is introduced into the same bottle subsequent to cleaning. Aromatic substances which have penetrated into the wall of a bottle are particularly likely to affect the taste of mineral water if such liquid is introduced into a bottle which was previously filled with a fruit juice or with an aromatized beverage. Even minute traces of an aromatic substance which was permitted to penetrate into the wall of a PET bottle and thereupon contacts a supply of mineral water are likely to impart to the mineral water a taste which need not necessarily be unpleasant but is nevertheless not to the liking of a person who desires to drink genuine mineral water.

Heretofore known bottle cleaning apparatus are incapable of properly and reliably cleaning bottles having walls wherein the intermolecular spaces are filled with diffused aromatic substances or with any other substances which are likely to enter a supply of beverage in the freshly cleaned bottle. On the other hand, it is not only desirable but also important and often critical to ensure that a bottle whose walls contain substances which are likely to contaminate a freshly introduced supply of liquid can be detected and segregated from satisfactory bottles. Therefore, the bottle filling industries employ a variety of inspecting apparatus which are intended to detect undesirable (including dangerous) substances (such as contaminants) and to thus ensure reliable segregation of unacceptable bottles from satisfactory bottles. For example, it is known to direct one or more beams of radiation against a bottle in such a way that the beam or beams penetrate through the opening and through the bottom end wall of the tested bottle. The intensity of a beam which issues from the bottle is monitored in order to draw conclusions regarding the quality of the tested container. Such procedure is satisfactory if one desires to ascertain the presence of relatively large foreign bodies, the presence of one or more contaminants and/or the presence of defects (e.g., damage to the internal surface of the bottom wall). However, minor defects are not likely to be detected by resorting to heretofore known inspecting apparatus. Moreover, such apparatus are incapable of detecting the presence of traces of undesirable substances which adhere to the internal surface of a plastic bottle or which have become diffused in the spaces between the molecules of plastic material adjacent the internal surface of a bottle. This also holds true for certain recent proposals (known as sniffing methods) which are intended to permit detection of substances likely to release aerosols in a plastic bottle. Moreover, such methods cannot be resorted to in connection with the testing of bottles in a high-speed bottle filling machine because the testing of a bottle takes up a relatively long interval of time. Still further, the reliability of such methods is questionable so that they cannot be resorted to in connection with the testing of bottles which are about to receive beverages and/or other substances intended for consumption by humans or animals.

OBJECTS OF THE INVENTION

An object of the invention is to provide a simple and inexpensive method which can be resorted to for predictable and reliable testing of plastic bottles and/or analogous containers prior to filling or refilling with a flowable substance.

Another object of the invention is to provide a method which renders it possible to reliably and rapidly detect minute quantities or traces of undesirable constituents which are likely to affect the taste, the appearance and/or other characteristics of the subsequently admitted flowable substance.

A further object of the invention is to provide a method which can be practiced for the testing of a wide variety of plastic bottles and/or analogous containers with the same degree of predictability and reliability.

An additional object of the invention is to provide a method which constitutes a substantial improvement over heretofore known methods of testing empty bottles or like containers prior to initial filling or prior to refilling.

Still another object of the invention is to provide a method which can be practiced by resorting to simple and compact apparatus.

A further object of the invention is to provide a method which can be resorted to for the classification of containers in accordance with their contents and/or to facilitate or ensure predictable segregation of unsatisfactory containers from acceptable containers.

Another object of the invention is to provide a simple, compact and reliable apparatus for the practice of the above outlined method.

An additional object of the invention is to provide the apparatus with novel and improved means for controlling the radiation which is utilized to test empty bottles or analogous containers.

Still another object of the invention is to provide the apparatus with novel and improved means for processing signals which are generated as a result of optical testing of radiation-transmitting containers.

A further object of the invention is to provide an apparatus which renders it possible to classify radiation-transmitting containers in accordance with the composition of the material of their walls.

Another object of the invention is to provide an apparatus which can be readily installed in modern bottle filling and capping machines, i.e., in machines which are designed to turn out large numbers of filled containers per unit of time.

An additional object of the invention is to provide a bottle filling plant which employs one or more apparatus of the above outlined character.

Still another object of the invention is to provide an apparatus which can be utilized for simultaneous detection of two or more flaws of radiation-transmitting containers.

SUMMARY OF THE INVENTION

One feature of the present invention resides in the provision of a method of optically testing radiation-transmitting containers, particularly colorless plastic bottles. The improved method comprises the steps of directing a beam of optical radiation upon a surface of a container to be tested whereby the surface scatters at least a portion of such radiation, monitoring the thus scattered radiation, and generating at least one signal denoting at least one characteristic of monitored radiation. The signal generating step can comprise analyzing and evaluating the scattered radiation.

The beam of optical radiation is preferably focussed upon a portion of the internal surface of the container to be tested, and the signal generating step of such method can include analyzing and evaluating radiation which is scattered by the aforementioned portion of the internal surface of the container which is being tested. Focussing ensures the development of intensive scattered radiation whenever the condition of the tested surface and/or the material at such surface (e.g., contaminants and/or other undesirable substances) warrants the development of intensive scattered radiation.

The radiation is preferably monochromatic radiation, and the scattered radiation can include the Raman spectrum of material at the surface of the container being tested. The signal generating step of such method comprises analyzing the Raman spectrum and producing at least one signal denoting at least one characteristic of the Raman spectrum. The at least one characteristic of the Raman spectrum is indicative of the quality of the container and/or of at least one constituent of the container in the region of the surface which scatters the radiation. The just outlined method can further comprise the steps of establishing and maintaining at least one reference signal denoting a specific Raman spectrum, comparing the at least one reference signal with the at least one signal denoting at least one characteristic of the first mentioned Raman spectrum (namely the spectrum of material at the surface of the container being tested), and producing at least one additional signal denoting the difference between the compared signals, and classifying the tested container as a function of (i.e., in dependency upon) the at least one additional signal. The method can further comprise the step of transporting a series of successive containers along a predetermined path (e.g., along an endless circular path), and the directing step of such method can include directing the beam of optical radiation upon the surfaces of successive containers in a predetermined portion of the path. The monitoring step of such method can include monitoring radiation which is scattered by the surfaces of successive containers in the path, and the signal generating step of such method can comprise producing a series of signals denoting the characteristics of Raman spectra of the material of successive containers. The comparing step of such method can comprise comparing the at least one reference signal with each of the series of signals and producing an additional signal for each of the series of signals. The classifying step of the just outlined method can comprise classifying the tested containers of the series of containers as a function of the respective additional signals.

A container to be tested can contain at least one substance which is adjacent the surface serving to scatter the radiation of the beam and causes scattering of optical radiation into resonance fluorescence. The monitoring step of the method of testing such containers can include detecting the scattered optical radiation and splitting the detected radiation to obtain a spectrum of fluorescence. The signal generating step of the just outlined method can include producing at least one signal which denotes at least one characteristic of the spectrum of fluorescence. The at least one characteristic can be indicative of the quality of the container in the region of its surface. The at least one characteristic of the spectrum can be indicative of at least one constituent of the container in the region of the surface serving to scatter the beam of radiation. The splitting step can include directing the scattered radiation against a diffraction grating. The just outlined method can further comprise the step of establishing and memorizing at least one reference signal denoting a specific spectrum of fluorescence, comparing the at least one reference signal with the at least one signal denoting the at least one characteristic of the first named fluorescence spectrum (of radiation which is scattered by the surface of the container being tested) and producing at least one additional signal which denotes the difference between the compared signals, and classifying the tested container as a function of the at least one additional signal. Such method can further comprise the step of transporting a series of successive containers along a predetermined path, and the directing step of such method can comprise directing the beam of optical radiation upon the surfaces of successive containers in a predetermined portion of the path. The monitoring step can include monitoring radiation which is scattered by the surfaces of successive containers in the path, and the signal generating step can include producing a series of signals which denote the characteristics of the spectra of fluorescence of successive containers of the series. The comparing step can include comparing the at least one reference signal with each of the series of signals and producing an additional signal for each of the series of signals. The classifying step of such method can include classifying the containers as acceptable and unacceptable containers in dependency on the characteristics (e.g., intensities) of the respective additional signals.

The scattered radiation can further include the Rayleigh spectrum of the material at the surface of the container being tested, and the method can further include the steps of monitoring the intensity of the Rayleigh spectrum and generating signals which denote the intensity of the Rayleigh spectrum.

The beam of optical radiation can be a laser beam.

The method can further comprise the step of transporting a series of successive containers along a predetermined path, and the directing step of such method can comprise focussing the beam upon the surfaces of successive containers in a predetermined portion of the path. The just outlined method can further comprise the step of changing the orientation of successive containers of the series in the predetermined portion of the path (e.g., by turning the containers about their central longitudinal axes) so that the beam is focussed upon a plurality of different portions of the surface of the container in the predetermined portion of the path. The signal generating step of such method can comprise producing a plurality of signals for each container, one for each of the plurality of different orientations. Such method can further comprise the step of averaging each plurality of signals to obtain an averaged signal for each of the series of successive containers.

Another feature of the present invention resides in the provision of an apparatus for testing radiation-transmitting containers, particularly colorless plastic bottles. The apparatus comprises a source of optical radiation, means for transporting a series of successive containers along a predetermined path (e.g., an endless circular path), means for directing a beam of radiation from the source against internal surfaces of successive containers of the series in a predetermined portion of the path whereby the internal surfaces of successive containers scatter at least a portion of the directed beam, means for monitoring the radiation which is scattered by the internal surfaces of successive containers, means for generating a succession of signals each of which denotes at least one characteristic of radiation scattered by the internal surfaces of successive containers, and control means including means for analyzing and evaluating the signals. The directing means can include means for focussing scattered radiation upon the monitoring means, and the source can constitute or include a source of monochromatic radiation, such as a laser which emits radiation in the optical wavelength range of the spectrum. The directing means can include means for focussing the beam of radiation upon portions of internal surfaces of successive containers in the predetermined portion of the path. The means for monitoring and the signal generating means can comprise at least one spectrometer, and such spectrometer can comprise a holographic grating and a CCD detector. The grating is preferably positioned to direct scattered radiation against the detector.

The means for analyzing and evaluating can comprise means for processing the signals, and such processing means can include means for evaluating the structure of the spectrum of scattered radiation and for generating signals which denote at least one qualitative characteristic and/or material at the internal surfaces of successive containers. Furthermore, the means for analyzing and evaluating can comprise at least one memory for at least one reference signal which denotes a specific characteristic of a container. Such analyzing and evaluating means can further comprise means for comparing the reference signal with each of the succession of signals and for generating additional signals which denote differences between the reference signal and each of the succession of signals. Still further, the apparatus can comprise means for classifying or for effecting a classification of tested containers as a function of the respective additional signals.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain presently preferred specific embodiments with reference to the accompanying drawing.

BRIEF DESCRIPTION OF THE DRAWING

The single Figure of the drawing is a particularly diagrammatic and partly horizontal sectional view of an apparatus which embodies the present invention and is designed to test a succession of round plastic bottles.

DESCRIPTION OF PREFERRED EMBODIMENTS

The drawing illustrates a portion of a bottle testing apparatus which embodies one form of the present invention and includes a transporting unit 1 for a series of successive plastic bottles 7, a testing unit 2, and a control unit 3 serving to evaluate, analyze and process signals which are transmitted by the testing unit.

The transporting unit 1 comprises a conveyor 4 in the form of an indexable turret which is rotatable about a vertical axis and is driven by a suitable prime mover to move successive bottles of the series to a testing station 8, namely to a predetermined portion of an endless circular path which is defined by the conveyor 4. The periphery of the turret 4 is provided with sockets or recesses 6 each of which can snugly receive a bottle 7. A properly positioned bottle rests on a discrete second conveyor in the form of a turntable 9 serving as a means for changing the orientation of a bottle 7 at the testing station 4, namely for turning the bottle about its vertical axis. the turntables 9 are mounted on an annular or otherwise configurated carrier 11 which is indexable with the turret 4.

The bottles 7 can constitute containers which are made of a colorless light-transmitting (particularly transparent) synthetic plastic material, such as PET. Each such bottle is assumed to be reusable to repeatedly receive supplies of identical flowable material (e.g., a beverage) or to receive different types of flowable substances (e.g., first a fruit juice and thereupon carbonated water or mineral water). Each of the illustrated bottles 7 is assumed to have undergone a cleaning treatment upstream of the testing station 8 and to be on its way to storage or to a bottle filling apparatus or machine downstream of the turret 4. The purpose of the novel testing apparatus including the units 1, 2 and 3 is to inspect successive bottles 7 between the cleaning and filling stations in order to permit classification of tested bottles, e.g., into bottles which are made of different plastic materials or glass and/or into acceptable and unsatisfactory bottles so that the unsatisfactory bottles can be segregated upstream of the filling or refilling station. Filling or refilling of tested (satisfactory) bottles is normally followed by capping, labelling, crating and/or other operations.

In many instances, prior utilization of the bottles 7 is not known. Moreover, it is not known whether or not the bottles 7 which have undergone a cleaning operation and are to be tested in accordance with the method and in the apparatus of the present invention were treated properly by the person or persons who purchased the bottles and their contents prior to returning empty or partially emptied bottles for transport through the cleaning apparatus. Therefore, an intensive testing of successive bottles 7 which are on their way from the cleaning to the filling or refilling station is of utmost importance. Such testing can involve inspection for the purposes of detecting the presence of mechanical defects (e.g., cracks) and/or for the purpose of detecting the presence or absence of certain undesirable substances which are likely to affect the quality of the flowable material to be admitted into tested bottles at the filling or refilling station. Spot checking of certain bottles of a series of bottles advancing from the cleaning station to the filling or refilling station does not suffice because such mode of testing would be likely to result in advancement of a rather high percentage of defective bottles to the filling or refilling station. As already mentioned above, the prior utilization and the prior contents of bottles 7 arriving at the testing station 8 are not known or are not known sufficiently to ensure reliable segregation of all defective bottles without thorough testing or inspection of each and every bottle which is being transported to the filling or refilling station.

The turret 4 of the transporting unit 1 is driven (indexed) in such a way that each bottle 7 which arrives at the testing station 8 remains at such station for an interval of time sufficing to ensure reliable and thorough testing by the unit 2. The testing can involve a single test or two or more successive tests which follow each other upon completed indexing of a bottle 7 about its own axis, i.e., upon completed starting and arresting of the respective turntable 9. The exact nature of the means for indexing successive turntables 9 about their own vertical axis, while the turntables are maintained at the testing station 8, forms no part of the present invention. The same holds true for the turret 4 and for the carrier 11 of the turntable 9. Such carrier can constitute a disc or a ring. If it is desired or necessary to repeatedly test each bottle 7 which has arrived at the testing station 8, the drive for the turntables 9 is set to index the turntable 9 at the station 8 through one or more predetermined angles while the turret 4 is at a standstill.

The testing unit 2 comprises a source 12 of monochromatic optical radiation, for example, a suitable laser. A presently preferred laser is a so-called Nd:YAG laser (ytrium-aluminum garnet laser which is doped with neodymium) with frequency duplication or triplication. The source 12 is capable of emitting a beam 21 of radiation in the ultraviolet range of the electromagnetic spectrum. It is equally possible to employ another suitable laser or another source of monochromatic radiation in the optical wavelength range, namely in the ultraviolet, visible or near infrared range of the electromagnetic spectrum.

The beam 21 which issues from the source 12 is deflected by a mirror 13 and is caused to pass through an interference filter 14 and thereupon through an optical system 16 (the illustrated optical system comprises a set of lenses) serving to focus (direct) the beam 21 upon the internal surface 17 of a bottle 7 at the testing station 8. Thus, a portion of the internal surface 17 of the bottle 7 which is held at the testing station 8 is located at the focal point of the optical system 16, i.e., at least the major part of the radiation issuing from the source 12 and forming the beam 21 is concentrated at the selected portion of the internal surface 17 of the bottle 7 which is maintained at the testing station 8. Only a relatively small (and preferably very small) portion or fraction 19 of the radiation constituting the beam 21 forms a reference beam which is reflected by the interference filter 14 and impinges upon a reference beam sensor 18. The latter generates a reference signal which is indicative of the intensity and/or other characteristics of the reference beam and transmits such signal to the control unit 3.

The internal surface 17 of the bottle 7 at the testing station 8 brings about a scattering of radiation forming the beam 21. The thus scattered radiation is intercepted by the optical system 16 and is reflected (twice) by the interference filter 14. The latter is designed to permit at least the major part of scattered monochromatic exciter radiation to pass therethrough but the filter 14 reflects radiation having wavelengths other than that of monochromatic radiation. This entails a spectral purification of the radiation forming the beam 21 in that the filter 14 intercepts light (e.g., light of the exciter plasma) which accompanies the beam 21 issuing from the source (laser) 12. At the same time, the interference filter 14 purifies the relatively weak scattered radiation which is scattered at the internal surface 17 of the bottle 7 at the testing station 8 because the relatively strong laser beam is free to pass through the filter 14 whereas the filter causes at least the major part of relatively weak reflected scattered radiation to be reflected again and causes the scattered radiation to ultimately reach a mirror 23. Repeated reflection of scattered radiation at the filter 14 is desirable in order to ensure the establishment of a more satisfactory filtering effect. Such scattered radiation can be reflected twice or more than twice.

The illustrated interference filter 14 can be replaced by or used jointly with other filters without departing from the spirit of the invention. For example, a filter which is used with or which replaces the illustrated interference filter 14 can be designed to weaken laser radiation which accompanies the scattered radiation but to permit transmission of all or nearly all radiation having a wavelength or wavelengths other than that of laser radiation, i.e., to permit passage of all or nearly all scattered radiation. The scattered radiation which is reflected by the filter 14 is directed against a mirror 22 which reflects such radiation back to the filter 14 and the latter then directs scattered radiation against the aforementioned mirror 23. The mirror 23 directs scattered radiation to a collector lens 24 which causes such radiation to pass through a slit or gap defined by a diaphragm 26 or an analogous device and on to a diffraction grating 27. The illustrated grating 27 can constitute a holographically produced concave grating which is capable of optically breaking up or splitting the incoming radiation before the radiation reaches a CCD-detector 28. The grating 27 images the spectrum onto the detector 28 which monitors the spectrum of scattered radiation and transmits one or more signals denoting the characteristic data of the spectrum. Such signal or signals are transmitted to the control unit 3.

If the radiation which is scattered by the internal surface 17 of a bottle 7 at the testing station 8 and is returned to impinge upon the optical system 16 contains at least some diffusely reflected radiation (the so-called scattered Rayleigh radiation), a portion of such radiation is deflected by the interference filter 14 against a sensor 29. The latter then transmits to the control unit 3 a signal denoting the intensity of such radiation.

The control unit 3 comprises a first processor 31 which serves to process signals from the CCD detector 28 (i.e., signals containing information pertaining to the monitored spectra). The control unit 3 further comprises a memory 32 for the storage of reference signals, namely signals denoting one or more characteristics of the spectrum of a particular substance. Still further, the control unit 3 comprises a second processor 33 which receives signals from the sensor 29, and a memory 34 for the storage of threshold values. The outputs of the processors 31 and 33 are connected with a regulating circuit 36 which is used to process (additional) signals from the processors 31, 33 and transmits further signals which can be used for the purposes of proper classification of tested bottles 7.

A bottle 7 which is about to be tested is advanced to and comes to a halt at the testing station 8. The radiation beam 21 which is emitted by the source 12 is focussed upon a selected portion of the internal surface 17 of the bottle 7 at the station 8 whereby the internal surface causes the development of scattered radiation having a plurality of components depending upon the characteristics of tested portion of the internal surface 17 as well as upon the substances which are contained in the wall of the bottle 7 adjacent the tested portion of the internal surface 17. For example, a turbid liquid is likely to form at the internal surface 17 a layer or film which causes a diffuse scattering (Rayleigh scattering) of radiation forming the beam 21. The phase and the wavelength of the Rayleigh radiation are the same as those of the radiation constituting the beam 21. A similar result is produced if the beam 21 impinges upon an internal surface 17 which has been roughened during prior use of a bottle 7, e.g., by an aggressive substance. A portion of the thus obtained Rayleigh radiation propagates itself from the internal surface, through the optical system 16 and into the path of propagation of the beam 21 toward the internal surface of the bottle at the station 8. Some of the Rayleigh radiation which has penetrated through and beyond the optical system 16 is reflected by the interference filter 14 as well as by the mirror 22, and the remaining Rayleigh radiation passes through the filter 14 to impinge upon the sensor 29. The sensor 29 generates a signal which denotes the intensity of Rayleigh radiation and is transmitted to the signal processor 33 of the control unit 3. The processor 33 compares the received signal with the threshold values which are stored in the memory 34. If the intensity of the signal which is furnished by the sensor 29 and is received by the processor 33 exceeds a given maximum threshold value, the processor 33 transmits a comparison signal (additional signal) which is processed by the circuit 36 and is used, in a manner not specifically shown in the drawing, to effect segregation of the respective bottle 7, e.g., expulsion from the corresponding socket 6 downstream of the testing station 8, to thus ensure that such bottle (which is to be classified as a defective bottle) cannot reach the filling or refilling station. Signals which are transmitted by the sensor 29 greatly enhance the reliability of the improved method and apparatus by ensuring reliable detection of bottles which contain undesirable substances in the walls or at the internal surfaces.

A second component of scattered radiation which develops as a result of impingement of the beam 21 upon the internal surface 17 of a bottle 7 at the testing station 8 constitutes the so-called Raman radiation which is attributable to the presence of one or more specific substances in the wall adjacent the tested portion of the internal surface 17 of the bottle 7 at the station 8. The thus developed Raman radiation is caused to pass through the optical system 16 toward the filter 14 and is deflected by this filter as well as by the mirrors 22 and 23 so that it impinges upon the optical element 24. The latter directs Raman radiation into the slit of the diaphragm 26 so that the radiation reaches the CCD detector 28 by way of the diffraction grating 27. As already mentioned before, the grating 27 can constitute a holographically obtained concave grating which is capable of projecting onto the detector 29 a linear spectrum that is shifted toward the longer wavelength region of the electromagnetic spectrum. The characteristic data of such spectrum which is imaged on the detector 28 are indicative of the material of the wall adjacent the tested portion of the internal surface 17 at the station 8 as well as of the presence of one or more foreign substances adhering to or contained in the material of the wall. The characteristic data of the lines forming the spectrum which is imaged on the detector 28 are transmitted to the processor 31. The memory 32, which is connected with the processor 31, stores information (reference signals) denoting the characteristics of lines forming part of the spectra of selected substances. For example, the memory 32 can store information pertaining to the spectra of household solvents, brush cleaning agents, acetone, thinners, insect killers and/or other plant protecting agents, and/or others. Furthermore, the memory 32 can store information which is characteristic of one or more Raman and/or fluorescence spectra of each of certain presently preferred plastic materials for the making of bottles. Such materials include PET, polyethylene, polyvinyl chloride, polypropylene, glass and others. It is further advisable to store in the memory 32 a reference signal denoting the spectral lines of an ideal or perfect wall, i.e., of a bottle which is in fully satisfactory condition in the region of that portion of the internal surface which is contacted by the beam 21 subsequent to penetration of such beam through the entirely satisfactory wall. The processor 31 compares the signals from the detector 28 with reference signals which are stored in the memory 32 and generates additional signals denoting the optimal or required classification of the tested bottles 7, e.g., according to their material, according to the nature of their defects (e.g., according to the undesirable substances at or on the internal surfaces) and/or whether or not the tested bottles are acceptable for filling or refilling. Signals from the processor 31 are evaluated in the circuit 36 whose signals are utilized for actual classification of the tested bottles. For example, the bottles can be classified in accordance with the detected defects. Furthermore, if the testing resulted in the generation of signals (from the detector 28) which are indicative of the presence of harmful substances, the additional signal at the output of the processor 31 induces the circuit 36 to produce a signal which is used for preferably automatic segregation of the respective bottle 7 from satisfactory bottles, i.e., the bottle which contains a harmful substance is prevented from reaching the filling or refilling station. If the testing resulted in the generation of a signal which denotes that the wall of the bottle 7 at the testing station 8 contains one or more aromatic substances, for example, that the internal surface of the bottle 7 at the station 8 carries a film containing an aromatic substance which was contained in the decanted liquid (i.e., in the body of liquid which was introduced into the same bottle during an earlier advancement through a filling or refilling station), the respective tested bottle can be diverted to another filling station at which the bottles are to receive the same liquid as during previous filling. Still further, signals which are processed at 31 can be utilized to classify the bottles 7 according to their materials, i.e., into plastic bottles and glass bottles and/or into two or more sets of plastic bottles consisting of different materials (such as PET, polyethylene, polyvinyl chloride, etc.).

The monitoring of Raman radiation ensures reliable detection of certain substances because the intensity of such radiation is sufficient to guarantee accurate monitoring by the spectrometer 26–28 and the transmission of adequate signals to the processor 31. Thus an (additional) signal from the processor 31 to the circuit 36 can be readily evaluated and used for the generation of signals which can be used to segregate a bottle whose scanning has resulted in the generation of Raman radiation having an intensity that warrants discarding of the respective bottle.

A preliminary stage of operation of the improved testing apparatus can be devoted to the analyzing of spectra of bottles whose materials are known, and the corresponding reference signals are thereupon stored in the memory 32 to be utilized for comparison with signals transmitted by the detector 28 in the course of actual testing of bottles 7 arriving directly from a washing or cleaning station.

A further component or constituent of radiation which has been scattered at the internal surface 17 of a bottle 7 coming to a halt at the testing station 8 is attributable to a fluorescence radiation developing as a result of impingement of the beam 21 upon certain substances in and/or at the surface 17. Such fluorescence radiation is guided in the same way as the aforediscussed Raman radiation, i.e., it is caused to impinge upon the grid 27 and to have its spectrum imaged onto the detector 28 or onto a second detector, e.g., a conventional diode line detector. The spectrum of the fluorescence radiation is shifted to a greater extent toward the long wavelength range of the electromagnetic spectrum; such spectrum is a continuous spectrum having a pronounced luminous intensity. Signals denoting the characteristics of fluorescent radiation are transmitted to the processor 31 to be processed in the same way as other signals generated by the detector 28 and denoting the characteristics of spectra imaged by the grid 27. A spectral analysis of fluorescent radiation furnishes information pertaining to the presence or absence of certain foreign substances including oils, propellants, fuels, pesticides, certain solvents and others. The improved apparatus can detect minute traces or concentrations of such foreign substances, for example, all the way down to the parts-per-billion range.

Fluorescence radiation is detected, monitored and analyzed in order to ascertain the presence of substances which cannot or cannot be reliably detected by analyzing the Raman radiation.

As already mentioned above, the evaluation of fluorescence radiation can be carried out by resorting to a discrete apparatus which is, or which can be, similar to that employed for the evaluation of scattered Raman radiation. In fact, it often suffices to evaluate only the fluorescence radiation and to disregard the scattered Raman and/or Rayleigh radiation.

The reference radiation 19 which is diverted from the beam 21 is used to generate in the sensor 18 a reference signal which can be utilized for accurate calibration and/or zeroing or zero setting of the processors 31 and 33.

In order to enhance the reliability of the improved method and apparatus, it is often advisable to test each bottle 7 of a series of successive bottles advancing toward and past the testing station 8 twice or even more than twice. This can be accomplished in a simple and time-saving manner by causing the drive means for the turntable 9 at the testing station 8 to change the orientation of the once tested bottle 7 through one or more angles of preselected magnitude. This renders it possible to test two or more portions of an internal surface, e.g., two portions which are located diametrically opposite each other or three portions which are equidistant from one another as seen in the circumferential direction of the bottle 7 at the testing station 8. If each bottle 7 is tested twice or more than twice, the control unit 3 is or can be designed to average the signals obtained during testing of a particular bottle so that the output of the circuit 36 transmits a single signal to the classifying and/or segregating means for tested bottles.

An important advantage of the improved method and apparatus is that they render it possible to reliably detect small as well as extremely small quantities of harmful substances and/or undesirable foreign substances. This is particularly desirable when the bottles 7 arriving at the testing station 8 are to be reused, i.e., such bottles have been transported through a washing or cleaning station in order to ensure that they are ready to receive metered quantities of a particular liquid which may but need not be the same as the previous contents of a reused bottle. Consequently, the improved method and apparatus ensure that all of the bottles which have been permitted to advance beyond the testing station 8 and to reach the filling or refilling station are actually suitable or acceptable for filling or refilling.

It is further within the purview of the invention to combine the improved apparatus with one or more conventional apparatus, e.g., with apparatus which are utilized to determine the presence or absence of other types of defects including the presence of relatively large foreign bodies in a container, the presence of cracks, chipped portions or similar damage, undue deformation of portions of or entire bottles, and/or others.

In lieu of or in addition to the aforedescribed presently preferred specific systems for the evaluation of Raman and fluorescence radiation, the improved method can also be carried out by resorting to other types of spectrometers. For example, the spectrometer including the parts 26, 27 and 28 can be replaced with a prism spectrometer, with an interferometer or with a spectrometer employing a graduated interference filter. It is equally possible to direct the beam of radiation issuing from the source 12 or from another suitable source by resorting to other types of beam directing means as long as the beam which reaches the internal surfaces of successive bottles at the testing station is capable of furnishing scattered Raman and fluorescence radiation.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A method of optically testing radiation-transmitting containers, particularly colorless plastic bottles, comprising the steps of directing a beam of monochromatic radiation upon a surface of a container to be tested, including focussing the beam upon a portion of an internal surface of the container to be tested, whereby the internal surface scatters at least a portion of said radiation and the thus scattered radiation includes the Raman spectrum of the material of the container at said internal surface; monitoring the scattered radiation; and generating at least one signal denoting the at least one characteristic of the monitored radiation, including analyzing the Raman spectrum and producing at least one signal denoting the at least one characteristic of such spectrum.

2. The method of claim 1, wherein said signal generating step includes evaluating the scattered radiation.

3. The method of claim 1, wherein said at least one characteristic of the Raman spectrum is indicative of the quality of the container in the region of said internal surface thereof.

4. The method of claim 1, wherein said at least one characteristic of the Raman spectrum is indicative of at least one constituent of the container in the region of said internal surface.

5. The method of claim 1, wherein said monitoring step includes directing the scattered radiation against a diffraction grating.

6. The method of claim 1, further comprising the steps of establishing and memorizing at least one reference signal denoting a specific Raman spectrum, comparing said at least one reference signal with said at least one signal denoting at least one characteristic of said first named spectrum and producing at least one additional signal denoting the difference between the compared signals, and classifying the tested container as a function of said at least one additional signal.

7. The method of claim 6, further comprising the step of transporting a series of successive containers along a predetermined path, said directing step including directing the beam of optical radiation upon the internal surfaces of successive containers in a predetermined portion of said path, said monitoring step including monitoring radiation which is scattered by the internal surfaces of successive containers in said path and said signal generating step including producing a series of signals denoting the characteristics of Raman spectra of the material of successive containers, said comparing step including comparing said at least one reference signal with each of said series of signals and producing an additional signal for each of said series of signals, said classifying step including classifying the tested containers of said series of containers as a function of the respective additional signals.

8. The method of claim 1, wherein the scattered radiation further includes the Rayleigh spectrum of the material at said internal surface, and further comprising the steps of monitoring the intensity of the Rayleigh spectrum, and generating signals denoting the intensity of the Rayleigh spectrum.

9. The method of claim 1, wherein the beam is a laser beam.

10. The method of claim 1, further comprising the step of transporting a series of successive containers along a predetermined path, said directing step including focussing said beam upon the internal surfaces of successive containers of said series in a predetermined portion of said path and further comprising the step of changing the orientation of successive containers of said series in said predetermined portion of said path so that said beam is focussed upon a plurality of different portions of the internal surface of the container in said portion of said path, said signal generating step including producing a plurality of signals for each container, one for each of said plurality of different orientations.

11. The method of claim 10, further comprising the step of averaging each plurality of signals.

12. Apparatus for optically testing radiation-transmitting containers, particularly colorless bottles, comprising a source of optical radiation; means for transporting a series of successive containers along a predetermined path; means for directing a beam of radiation from said source against portions of internal surfaces of successive containers of said series in a predetermined portion of said path whereby the irradiated portions of the internal surfaces and the material adjacent the irradiated portions of the internal surfaces of successive containers scatter at least a portion of the directed beam; means for monitoring the radiation which is scattered at the internal surfaces of successive containers; means for generating a succession of signals each denoting at least one characteristic of radiation scattered at the internal surfaces of successive containers; and means for analyzing and evaluating said signals.

13. The apparatus of claim 12, wherein said directing means includes means for focussing scattered radiation upon said monitoring means.

14. The apparatus of claim 12, wherein said source includes a source of monochromatic radiation.

15. The apparatus of claim 12, wherein said source includes a laser which emits radiation in the optical wavelength range of the spectrum.

16. The apparatus of claim 12, wherein said means for monitoring and said signal generating means comprise at least one spectrometer.

17. The apparatus of claim 16, wherein said at least one spectrometer comprises a holographic grid and a CCD detector, said grid being positioned to direct scattered radiation against said detector.

18. The apparatus of claim 12, wherein said means for analyzing and evaluating comprises means for processing said signals including means for evaluating the structure of the spectrum of scattered radiation and for generating signals denoting at least one qualitative characteristic and/or material at the internal surfaces of successive containers of said series.

19. The apparatus of claim 12, wherein said means for analyzing and evaluating comprises at least one memory for at least one reference signal denoting a specific characteristic of a container, and means for comparing said reference signal with each of said succession of signals and for generating additional signals denoting differences between said reference signal and each of said succession of signals.

20. The apparatus of claim 19, further comprising means for classifying tested containers as a function of the respective additional signals.

21. A method of optically testing a radiation-transmitting container, particularly a colorless bottle, having an internal surface and containing at said internal surface at least one substance which causes scattering of optical radiation into resonance fluorescence, comprising the steps of directing a beam of optical radiation upon the internal surface of the container whereby the surface scatters at least a portion of said radiation; monitoring the thus scattered radiation, including detecting the scattered optical radiation and splitting the detected radiation to obtain a spectrum of fluorescence; and generating at least one signal denoting at least one characteristic of monitored radiation, including producing at least one signal which denotes at least one characteristic of said spectrum.

22. The method of claim 21, wherein said at least one characteristic of the spectrum is indicative of the quality of the container in the region of said internal surface.

23. The method of claim 21, wherein said at least one characteristic of the spectrum is indicative of at least one constituent of the container in the region of said internal surface.

24. The method of claim 21, wherein said splitting step includes directing the scattered optical radiation against a diffraction grating.

25. The method of claim 21, further comprising the steps of establishing and memorizing at least one reference signal denoting a specific spectrum of fluorescence, comparing said at least one reference signal with said at least one signal denoting said at least one characteristic of said first named spectrum and producing at least one additional signal denoting the difference between the compared signals, and classifying the tested container as a function of said at least one additional signal.

26. The method of claim 25, further comprising the step of transporting a series of successive containers along a predetermined path, said directing step including directing said beam of optical radiation upon the surfaces of successive containers in a predetermined portion of said path, said monitoring step including monitoring radiation which is scattered by the surfaces of successive containers in said path, said signal generating step including producing a series of signals denoting the characteristics of spectra of fluorescence of successive containers of said series, said comparing step including comparing said at least one reference signal with each of said series of signals and producing an additional signal for each of said series of signals, said classifying step including classifying the tested containers of said series of containers as acceptable and unacceptable containers as a function of the respective additional signals.

* * * * *